United States Patent [19]

Craine et al.

[11] Patent Number: 5,361,771
[45] Date of Patent: Nov. 8, 1994

[54] PORTABLE PULMONARY FUNCTION TESTING DEVICE AND METHOD

[75] Inventors: Brian L. Craine, Fairfax, Calif.; Eric R. Craine, Tucson, Ariz.

[73] Assignee: Western Research Company, Inc., Tucson, Ariz.

[21] Appl. No.: 27,048

[22] Filed: Mar. 5, 1993

[51] Int. Cl.$^5$ .............................................. A61B 5/08
[52] U.S. Cl. .................................. 128/719; 128/725; 128/730; 73/23.3
[58] Field of Search ............... 128/716, 719, 725, 730; 73/23.3

[56] References Cited

U.S. PATENT DOCUMENTS

| | | | |
|---|---|---|---|
| 3,507,146 | 4/1970 | Campbell et al. | 73/23 |
| 3,910,261 | 10/1975 | Ragsdale et al. | 128/2.07 |
| 4,958,075 | 9/1990 | Mace et al. | 250/343 |
| 5,022,406 | 6/1991 | Tomlinson | 128/719 |
| 5,046,491 | 9/1991 | Derrick | 128/200 |
| 5,111,827 | 5/1992 | Rantala | 128/719 |
| 5,193,551 | 3/1993 | Pilipski | 128/719 |
| 5,197,481 | 3/1993 | Fisher | 128/719 |

FOREIGN PATENT DOCUMENTS 0740228 10/1978 U.S.S.R. .

OTHER PUBLICATIONS

Hauck, *Computer-aided Measuring System for Investigating the Uptake of Carbon Monoxide via the Respiration*, 1979, Biomed Techn. 24(1979) pp. 82–88.

Berecz et al., *Respiration Mass Spectrometer*, Medicor News (Hungry) No. 1 (1976), pp. 9–12.

Primary Examiner—Lee S. Cohen
Assistant Examiner—Brian M. Green
Attorney, Agent, or Firm—Cahill, Sutton & Thomas

[57] ABSTRACT

Early detection of lung dysfunction, which in HIV positive patients usually indicates PCP pneumonia infection, is accomplished by a CO fractional uptake test which includes supplying air containing 0.1% CO into a gas reservoir or regulator from which it is drawn through a non-rebreather valve into a mouthpiece and inhaled into the lungs of a patient. Exhaled air is directed by the non-rebreather valve into a chamber coupled to a gas inlet of an infrared CO analyzer. An end tidal volume of gas last exhaled by the patient is drawn through the CO analyzer which measures the concentration of CO therein. The concentration of CO in the air from the gas reservoir also is measured. The fractional uptake of CO is computed as a function of the patient's breathing rate and the minute volume and compared with a stored baseline value for the patient to determine the presence of or extent of lung dysfunction.

23 Claims, 2 Drawing Sheets

PORTABLE PULMONARY FUNCTION TESTING DEVICE AND METHOD

BACKGROUND OF THE INVENTION

The invention relates to a device and method for early, inexpensive outpatient evaluation of lung dysfunction, especially lung dysfunction that may be related to PCP pneumonia in HIV positive patients.

PCP pneumonia (pneumocystis carinii pneumonia) is caused by a microscopic organism that grows in the human lungs. It is a serious, opportunistic infection that occurs primarily in immunocompromised persons, and is the most prevalent and most life threatening infection occurring from patients' suffering from AIDS (Acquired Immune Deficiency Syndrome). More than 80 percent of AIDS patients will suffer from PCP pneumonia, and about 60 percent of AIDS patients' experience PCP pneumonia as their first major sign of AIDS. PCP pneumonia is characterized by fever, nonproductive cough and dyspnea on exertion. Chest x-rays may be normal or show a nonspecific pattern of interstitial infiltrates. A gallium scan may be positive but nonspecific. Arterial blood gas may show an abnormally low $PO_2$ ($PO_2$ is the partial pressure of oxygen in the arterial blood). The lung diffusion capacity ($DL_{CO}$) may be abnormally low, as well as the $O_2$ saturation measured by pulse oximetry after exercise. AIDS patients or HIV positive patients whose immune systems have been damaged frequently die from PCP pneumonia. Their lives could be lengthened, the quality of their life could be improved, and the expense of their treatment could be greatly reduced by early detection of the onset of PCP pneumonia. PCP pneumonia in AIDS patients often is not diagnosed in hospitals, as hospitalization generally is undesirable for AIDS patients because they are likely to be infected by many diseases that are present in the hospital because of their compromised immune systems.

Although a prior lung diffusion capacity test device is available in some hospitals, it is large and expensive, and rarely is used to diagnose PCP pneumonia in AIDS patients. This test is known as the "lung diffusion capacity measured for carbon monoxide" test, designated herein as the "$DL_{CO}$ test". There are several known methods of making the $DL_{CO}$ measurement, which is a strong indicator of a PCP infection within an HIV patient. Despite the potential importance of this test, it is not routinely utilized in most hospitals. This is due to (1) the low capacity of most pulmonary function laboratories, (2) reluctance to contaminate the $DL_{CO}$ test instruments used by testing AIDS patients, (3) the high cost, (4) the lack of availability of the $DL_{CO}$ test equipment in emergency rooms, and (5) the inefficiency of sending a patient, especially an AIDS patient, from one clinic to another for testing. It should be appreciated that any time hospital equipment is used in contact with AIDS patients, it must be sterilized before and after use. Such sterilization is time consuming and expensive, and is performed as infrequently as possible.

Historically, AIDS patients have been first diagnosed as having PCP pneumonia when they arrive in a hospital emergency room. In the event such a patient is determined to have PCP pneumonia, the patient is likely to be placed in an intensive care unit for several weeks or more, at a cost of $30,000 to $50,000. Treatment of PCP pneumonia presently is the largest cost component of care of AIDS patients. The death rate of AIDS patients due to PCP pneumonia at this state is approximately 30 percent. If the AIDS patient lives, further treatment costs are very high.

Thus, it is critical that there be an early assessment of the likelihood of a PCP infection in known or suspected HIV positive patients.

It is known that AIDS patients with the longest survival are those in which the occurrence of PCP pneumonia is diagnosed early in the disease progression. A common treatment for PCP pneumonia in AIDS patients is use of BACTRIM or intravenous pentamidine. These drugs are quite toxic, and although they alleviate symptoms of PCP pneumonia, if the patient survives for a long time the toxic side effects can become serious. Early diagnosis of PCP pneumonia would allow less toxic doses of these drugs to be used.

Thus, there is an urgent need for an improved, inexpensive, portable apparatus and associated method for early detection of lung dysfunction, especially in HIV positive patients, and especially to help in early diagnosis of PCP pneumonia in AIDS patients.

Physicians generally realize that excessive amounts of the foregoing drugs often are administered to PCP pneumonia patients. It would be highly desirable for physicians to be able to have an objective basis for better judging the dosages and durations of administering such drugs to PCP pneumonia patients, to reduce the toxic side effects thereof.

There are circumstances in which it is desirable to obtain accurate measurements of the amount of CO contained in exhaled breath of a patient, worker, etc. For example, during pre-natal care it may be desirable to determine if an expectant mother is telling the truth when she states that she has not been smoking. Or, in various industrial working environments, it may be desirable to accurately determine the amount of damage that has been done to the person's lungs by such environment. The fractional uptake of CO subsequently described can indicate the amount of such lung damage.

Accordingly, it would be desirable to have an economical method and apparatus for measuring the amount of CO in a person's exhaled breath.

SUMMARY OF THE INVENTION

Accordingly, it is an object of the invention to provide a portable system and technique for inexpensive and accurate early detection of lung dysfunction, especially in HIV positive patients and in other patients whose immune systems have been compromised.

It is another object of the invention to provide a practical way of measuring lung function on an outpatient basis.

It is another object of the invention to provide an inexpensive technique for determining if excessive CO has been recently inhaled by a person.

It is another object of the invention to provide a technique for determining the extent of lung damage caused by toxic environmental conditions in a patient.

It is another object of the invention to provide an inexpensive system that can measure fractional uptake of CO on the basis of either end tidal volume or "mixed" collected exhaled gas volume.

It is another object of the invention to provide a system and technique for correcting fractional uptake of CO on the basis of measurements of minute volume and respiratory rate of the patient.

Briefly described, and in accordance with one embodiment thereof, the invention provides a method of detecting lung dysfunction, especially that caused by PCP pneumonia including supplying air containing a first concentration of CO (carbon monoxide). A non-rebreather valve is operated in response to inhalation effort by the patient, allowing the air to be inhaled by the patient through a mouthpiece. The non-rebreather valve closes in response to exhalation by the patient, causing exhaled gas to flow through the non-rebreather valve and through a gas exhalation chamber, part of the exhaled air being exhausted to the atmosphere, the last portion including an end tidal volume remaining in the exhaled gas chamber. During the next inhalation, a pump draws the end tidal volume of exhaled gas through a CO analyzer. A first digital signal is produced to represent the concentration of CO in the end tidal volume. The CO concentration of the air supplied to the patient is measured by passing a portion of it through the CO analyzer and producing a second digital signal representing the concentration of CO in the supplied air. The fractional uptake of CO from the first and second digital signals is computed and compared with a stored baseline fractional uptake value previously obtained for the patient or a population norm for functional uptake of CO. A host computer computes the fractional uptake of carbon monoxide according to the expression $$FU(CO)_{et} = \frac{F_I - F_A}{F_I} = 1 - \frac{F_A}{F_I}$$

where $F_I$ is the CO percentage concentration of gas to be inhaled and $F_A$ is the CO percentage concentration of the end tidal volume gas exhaled. In the described embodiment, the fractional uptake is corrected for minute volume, age, and sex. The patient is determined to have a lung dysfunction if the present fractional uptake is below the baseline fractional uptake by a predetermined amount. In the described embodiment of the invention the first concentration is 0.1%. In one described embodiment, an exhalation chamber has a volume at least equal to a desired "end tidal volume" of breath last exhaled by the patient. A negative pressure is produced at an output of the CO monitor by means of a pump turned on by the patient's every attempt to inhale, to draw the end tidal volume through the CO monitor.

In accordance with another embodiment of the invention, a patient or worker who has breathed CO containing air, for example by smoking cigarettes, exhales into the mouthpiece. The computer reads the CO concentration in gas exhaled by the patient or worker from the output of the CO analyzer. The normal or baseline CO concentration in air exhaled by a population may be previously established. The present CO concentration reading may be compared with the baseline to determine, for example, if the person has been smoking, if CO concentration in the work place air exceeds a predetermined level, or if significant lung damage has occurred due, for example, to toxic environmental conditions. In another embodiment of the invention, fractional uptake computations are compared to preestablished baseline data to allow physicians to better determine drug dosages in treatment of PCP pneumonia or other lung disease.

In accordance with another embodiment of the invention, the disclosed apparatus includes a pneumotachometer connected to measure the breathing rate of the patient. Measurements of the minute volume are used to adjust the computed fractional uptake of carbon monoxide to account for these factors. In another embodiment of the invention, a mixture of all air exhaled by the patient is collected and utilized, instead of just the end tidal volume to enable the disclosed apparatus to compute fractional uptake of carbon monoxide on the basis of either end tidal volume or mixed exhaled air.

DETAILED DESCRIPTION OF THE PREFERRED EMBODIMENTS OF THE INVENTION

Figure 1:
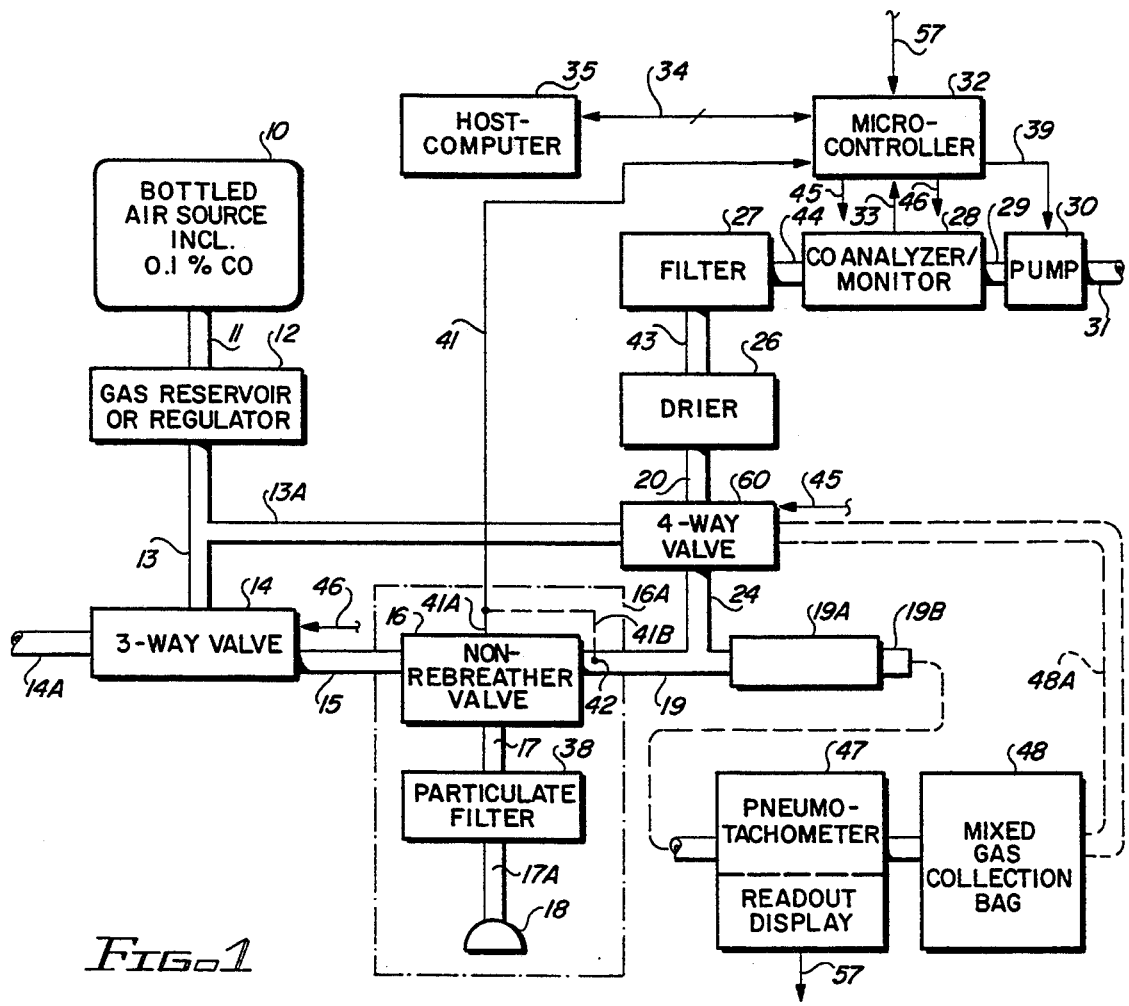
FIG. 1 is a block diagram of the PCP pneumonia detection device of the present invention.

As is indicated above, the diffusion capacity of the human lung is a measurable characteristic which is particularly useful for the determination of loss of lung function in interstitial lung disease and in the evaluation of PCP pneumonia. The diffusion capacity is most commonly evaluated as the "single breath diffusion capacity" ($DL_{sb}$). However, this test requires erroneous assumptions about lung function. It also requires expensive equipment, and specialized testing to obtain accurate measurements. In contrast, the "fractional uptake of CO" described below is simple to perform, does not depend on questionable assumptions about lung function, and can be accomplished with simpler equipment.

The traditional fractional uptake of CO (designated FU(CO) and (defined as $1-F_E/F_I$, where $F_E$ is the CO concentration of all expired air and $F_I$ is inspired CO concentration) has its own drawbacks, being sensitive to dead volume ($V_D$) (dead volume includes volume in the measurement instrumentation and anatomical volume through which air passes other than the lungs) and consequently being affected by respiratory rate, instrument dead space, and changes in $V_D$ which occur during exercise or increased work of breathing.

The alveolar uptake fraction (AU) is a measure of the uptake of CO at the alveolar level which is calculated from the FU(CO) and the dead volume. The AU is a constant value (dependent only upon the true diffusion constant) unaffected by dead volume and respiratory rate. The AU requires additional measurements and is more complicated to obtain than the traditional FU(CO).

We introduce the measurement of a new fractional uptake designated as the "end tidal uptake" of carbon monoxide, or $FU(CO)_{et}$. The $FU(CO)_{et}$ is defined by the equation $$FU(CO)_{et} = 1 - \frac{F_A}{F_I} \qquad \text{(Eq. 1)}$$

where $F_A$ is the end tidal concentration of CO gas and $F_I$ is the inspired concentration of CO gas.

The end tidal volume measurement of CO is different from the conventional fractional uptake measurement of carbon monoxide because the former includes only that gas that has been in the lung in contact with the alveolar membranes for the longest period of time. Typically, this includes approximately the last three percent of the subject's exhalation for reading by the CO analyzer 28 of FIG. 1.

As subsequently explained, we believe that the end tidal fractional uptake measurement provides more precision than the conventional fractional uptake measurement. Eventually, the procedure and equipment may be refined to the point where accurate measurements of end tidal volume fractional uptake of carbon monoxide can be made with just a few breaths by the patient.

The $FU(CO)_{et}$ has also been shown to be related to minute volume by the following equation:

$$FU(CO)_{et} = k - m*MV, \quad (Eq.\ 2)$$

where k and m are constants and MV is the minute volume.

This formula indicates that the $FU(CO)_{et}$ value is a linear function of minute volume only, and is generally independent of dead volume $V_D$ and respiratory rate. Equation (2) is valid for an individual or a population of individuals of the same sex and age. Furthermore, the constant k is the same for individuals of different ages and sex, within the error of measurement, and represents a "universal intercept constant" which is of practical use. We have determined the value of k to be approximately 78.

The effects of a number of parameters on the CO uptake were determined empirically. The parameters considered included minute volume, respiratory rate, tidal volume, body surface area, height, and weight of the subject. The value of $FU(CO)_{et}$ was measured repeatedly for different subjects under different conditions of exercise or hyperventilation to alter minute volume and respiratory rate over a suitable range. A multi-sample linear regression analysis was performed to determine which factors were of significance. The results of this analysis indicated that the most significant factors were minute volume and respiratory rate.

Our data indicate that during exercise the value of $FU(CO)_{et}$ is linearly dependent on minute volume regardless of whether minute volume is increased due to an increase in respiratory rate, tidal volume, or both, and that $FU(CO)_{et}$ is independent of respiratory rate and independent upon dead volume. Thus, the value of $FU(CO)_{et}$ is only a function of minute volume, in contrast to the other mentioned methods which are sensitive to instrument dead volume, anatomic dead volume, respiratory rate, subject height, and breath holding time. The minute volume is easily measured during testing by means of pneumotachometer 47.

The values of $FU(CO)_{et}$ can be interpreted in different ways including (a) comparison to population normals, (b) comparison to a patient's normal values, or (c) by inclusion of a universal intercept point with the patient's normal values. These different ways are discussed below.

Comparison with population normal values can be accomplished by determining a population linear regression line for $FU(CO)_{et}$ values as a function of minute volume. The linear regression allows for the determination of the value of $FU(CO)_{et}$ at the subject's minute volume and the standard deviation of error at that minute volume. The patient's $FU(CO)_{et}$ can then be expressed as a standard deviation from the normal.

Comparison to a patient's normal values can be accomplished in the same manner as described for the population normals, except that a linear regression line of the patient's own prior $FU(CO)_{et}$ values are used to determine the value and the standard deviation of error of the $FU(CO)_{et}$ at a particular presently measured value of the patient's minute volume. The patient's present $FU(CO)_{et}$ can then be expressed as a standard deviation from their own previously determined "normal" value at the patient's present minute volume. In practice this requires a minimum of about three normal values obtained when the patient is healthy.

Comparison to a patient's normal values with the inclusion of a universal intercept point is accomplished the same as for comparison to a patient's normal values except that an intercept point corresponding to a MV of 0 is included in the calculation of the linear regression curve. Empirical testing has indicated that the intercept point is the same, within error, for groups that even have different lung diffusion constants. That value is about 78. Since this number is determined from a large number of individuals it is statistically very accurate and may make the calculation of a patient's linear regression curve more accurate, particularly with a small number of normal values. The patient's $FU(CO)_{et}$ can then be expressed as a standard deviation from his or her own normal values including the universal intercept point.

FIG. 1 is a diagram of a system that could be used to perform this test. A source of air containing precisely 0.1% (or other fixed percentage) CO (carbon monoxide) is supplied through tube 11 into a gas reservoir bag (or gas flow regulator) 12. Gas reservoir or regulator 12 is connected by tube 13 to one port of a 3-way valve 14. Another port of 3-way valve 14 is connected by tube 14A to the ambient atmosphere, and a third port of valve 14 is connected by tube 15 to one port of a non-rebreather valve 16. Non-rebreather valve 16 has another port connected by tube 17, filter 38, and tube 17A to a mouthpiece 18 through which a patient being tested inhales and exhales, using a nose clip to prevent any breathing through his nose. The air containing 0.1% CO can flow through 3-way valve 14 to allow gas from reservoir bag 12 to be inhaled by the patient through non-rebreather valve 16, filter 38, and mouthpiece 18.

A third port of non-rebreather valve 16 is connected by tube 19 to a gas container 19A. Container 19A is of sufficient volume to contain an "end tidal volume" of air last exhaled by the patient. Gas container 19A is connected by exhaust tube 19B to the ambient atmosphere.

In one embodiment of the invention, as shown in FIG. 1, tube 19B can be connected to the inlet of a pneumotachometer 47. A pneumotachometer is a device which measures the respiratory rate of the person, that is, the number of breaths per minute, and also records the volume of each breath in liters. From these measurements, the "minute volume" (the volume of air that is moving through the pneumotachometer in one minute) can be computed. We have found that the fractional uptake of carbon monoxide measurement depends on how much volume of air the patient is pushing through his or her lungs. For example, in a person who is hyperventilating, the large volume of air moving through his or her lungs has little time to interact with the lung membranes, resulting in inefficient transfer of CO to the lungs, resulting in a modified fractional uptake of carbon monoxide. (A suitable pneumotachometer can be a model MAGTRACK II, commercially available from Ferraris Medical, Inc. of Holland, N.Y.) Pneumotachometer 47 may produce signals 57 which are read by microcontroller 32 to allow microcontroller 32 or host computer 35 to make the above mentioned minute volume computation. Alternatively, the pneumotachometer 47 can be visually read and the results can be manually input to microcontroller 32 or host computer 35.

An outlet of pneumotachometer 47 may be connected by a suitable tube to an inlet of a sealed gas collection bag 48. The use of the gas collection bag 48 allows collection of a mixture of all air, including end tidal volumes, exhaled by the patient. The exhaled gas collected in bag 48 then can be used to measure conventional fractional uptake FU(CO) by setting 4-way valve 60 to route gas from a tube indicated by dotted line 48A connecting an outlet of bag 48 to a port of 4-way valve 60.

When the patient exhales, a flapper in non-rebreather valve 16 automatically closes off an internal path to tube 15, allowing exhaled air to pass through tube 19 into chamber 19A, out of exhaust port 19B, through pneumotachometer 47 and into gas collection bag 48, if the latter two elements are used.

Tube 13 has a port connected by tube 13A to one port of 4-way valve 60. Tube 19 has a port connected by tube 24 to a second port of 4-way valve 60. A third port of 4-way valve 60 is connected by tube 20 to the inlet of a dryer 26, the outlet of which is connected by tube 43 to an inlet of a hydrophilic filter 27. The outlet of filter 27 is connected by a tube 44 to an inlet of CO analyzer/monitor 28. The gas outlet of CO analyzer 28 is connected by tube 29 to an inlet of a pump 30, the outlet of which is connected to the ambient atmosphere by exhaust tube 31.

CO analyzer 28 continually produces analog output signals on conductor 33 representing the CO concentration of the gas present in CO analyzer 28. The analog signals 33 are applied as inputs to a microcontroller 32. Microcontroller 32 converts analog signal 33 into digital signals in a standard RS232 format and supplies them via bus 34 to an RS232 input of host computer 35, which can be any conventional personal computer or the like. Microcontroller 32 generates a control signal on conductor 39 connected to a switch of pump 30, and also generates control signals 45 and 46 to control 4-way valves 60 and 3-way valves 14, respectively. Alternatively, 4-way valve 60 and 3-way valve 14 can be manually operable valves. Manual valves are considerably less expensive than electrically operated valves.

A signal 41 applied to an input of microcontroller 32 indicates whether the patient is inhaling or exhaling through mouthpiece 18. The signal 41 can be produced in a variety of ways. For example, dotted line 41A designates a conductor connected to an optical or electrical mechanical device (not shown) in non-rebreather valve 16 to detect the position of the flapper valve therein. Alternately, a pressure sensor 42 can be provided in the exhaust port of rebreather valve 16, producing a signal on a conductor indicated by dotted line 41B that indicates when increased pressure is present in tube 19. In any case, signal 41 causes microcontroller 32 to turn off pump 30 while the patient is exhaling and turning on pump 30 while the patient is inhaling.

When pump 30 is turned on, it draws the end tidal volume amount of previously exhaled gas in exhalation chamber 19A through tube 24, 4-way valve 60, dryer 26, filter 37, and into CO analyzer 28, so that the signal on conductor 33 represents the CO concentration in the end tidal volume of air last exhaled by the patient.

Before host computer 35 can compute the fractional uptake of CO, it first must obtain an accurate reading of the CO concentration in the gas supplied by gas bottle 10. Host computer 35 does this by causing microcontroller 32 to actuate 3-way valve 14 to block the port connected to tube 14A and provide a passage from tube 13A to tube 20. Microcontroller 32 then turns on pump 30, causing the air from gas reservoir or regulator 12 to be drawn through CO analyzer 28. The signal on conductor 33 then represents the CO concentration of that air. (As a practical matter, a suitable number of readings are averaged to obtain a more accurate value of the CO concentration of gas supplied by gas bottle 10.)

After host computer 35 has received the digital data on bus 34 representing the CO concentration in the standardized 0.1% CO air supplied by modeled air source 10, it then compares the level of carbon monoxide in the end tidal volume of air last exhaled by the patient with the level of carbon monoxide present in the air supplied by gas source 10. The ratio of the two CO concentrations is believed to be very significant, because carbon monoxide gas in a persons lungs is absorbed through alveolar membranes considerably less efficiently if the person has PCP pneumonia (or other lung dysfunction) than if he or she does not. Consequently, the above indicated measurement is capable of providing very early diagnosis of PCP pneumonia. Monitoring of the patient by the above system also may provide a reliable indicator of how far the PCP pneumonia has progressed.

The program executed by host computer 35 has the capability of measuring and displaying the CO concentration and displaying the results in real time, so that the operator can visually determine when the CO measurement has stabilized and instruct host computer 35 (via it's keyboard or a mouse) to "accept" the most recent computation and store it.

Figure 2A:
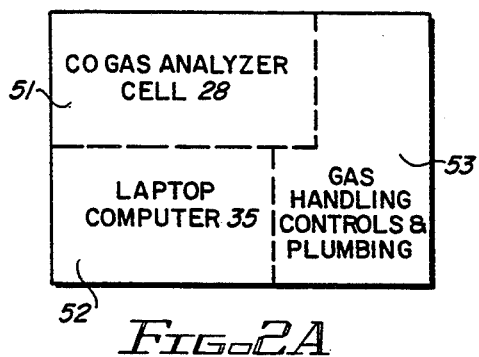
FIGS. 2A-2C show top, front, and left side diagrams that roughly illustrate a physical structure of the fractional uptake measuring system of FIG. 1.
Figure 2B:
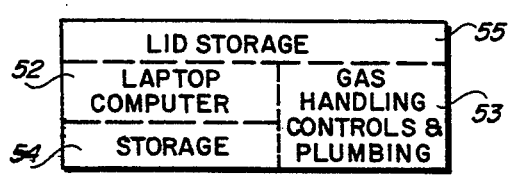
Figure 2C:
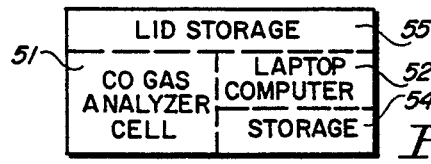

FIG. 2A shows a top view of a housing for the system shown in FIG. 1. The housing has the size and shape of a large briefcase or a small suitcase. FIG. 2B shows a front view thereof, and FIG. 2C which shows an end view. The dotted lines generally outline presently preferred locations of the main physical components of the system. More specifically, numeral 51 designates the general location of CO gas analyzer 28. Numeral 52 designates the location in which the laptop host computer 35 rests. Numeral 53 designates the location of the various valves and tubing of FIG. 1. Numeral 54 designates storage space for documents, patient needs, and the like. Numeral 55 designates available storage space in the hinged lid of the housing. Gas bottle 10 is external to the housing shown in FIGS. 2A–C.

Non-rebreather valve 16, tube 17, filter 38, tube 17A, and mouthpiece shown in FIG. 1 can be manufactured as a disposable unit 16A. Disposable unit 16A can be sealed in a sterile wrap, and a suitable number of them can be stored in storage space 54.

The 0.1% CO gas source is commercially available from Warren E. Collins, Inc. (Massachusetts). It supplies a 0.1% CO, 21% $O_2$, balanced $N_2$ test mixture prepared for pulmonary function testing. This test gas is dispensed through a standard Collins DS Model $CO_2$ regulator and is valved to gas reservoir bag 12.

A prototype fractional uptake monitor manufactured by Western Research Company, Inc. includes an instrument interface designed to provide power, control and communication for a single channel Andros ™ gas analysis cell which includes a chopped infrared light source, an absorption tube, a pyro-electric detector, and signal conditioning electronics. The instrument interface includes a power source that supplies ±12 volts DC and 24 volts AC, a 12-bit analog-to-digital converter (Analog Devices AD574A) and a single chip Motorola MC68705P3 microcomputer to convert the analog signal output into a serial RS-232-compatible form for communication via bus 34 to a host personal computer 35. The host computer preferably is a laptop microcomputer.

In operation, the patient is seated, and, with a nose clip in place, breathes air through the $FU(CO)_{et}$ monitor mouthpiece 18 for several minutes. The operator directing the measurement is prompted by host computer 35, which keeps track of time limits during the measurement. The subject is instructed to exhale normally, and then the 0.1% CO test gas is valved into mouthpiece 18. The subject breathes the test gas until the CO monitor 28 obtains a stable reading or until a time limit of several minutes has been reached. The subject's minute volume then is entered or input into microcontroller 32 or host computer 35. The subject then is "decoupled" from an analyzer 28, which then measures the CO concentration in the test gas and the concentration in the expired gas at equilibrium. The instrument averages a suitable number of readings to arrive at each concentration and then calculates the value of Equation (2) above, ie $$FU(CO)_{et} = 1 - \frac{F_A}{F_I}.$$

Figure 3:
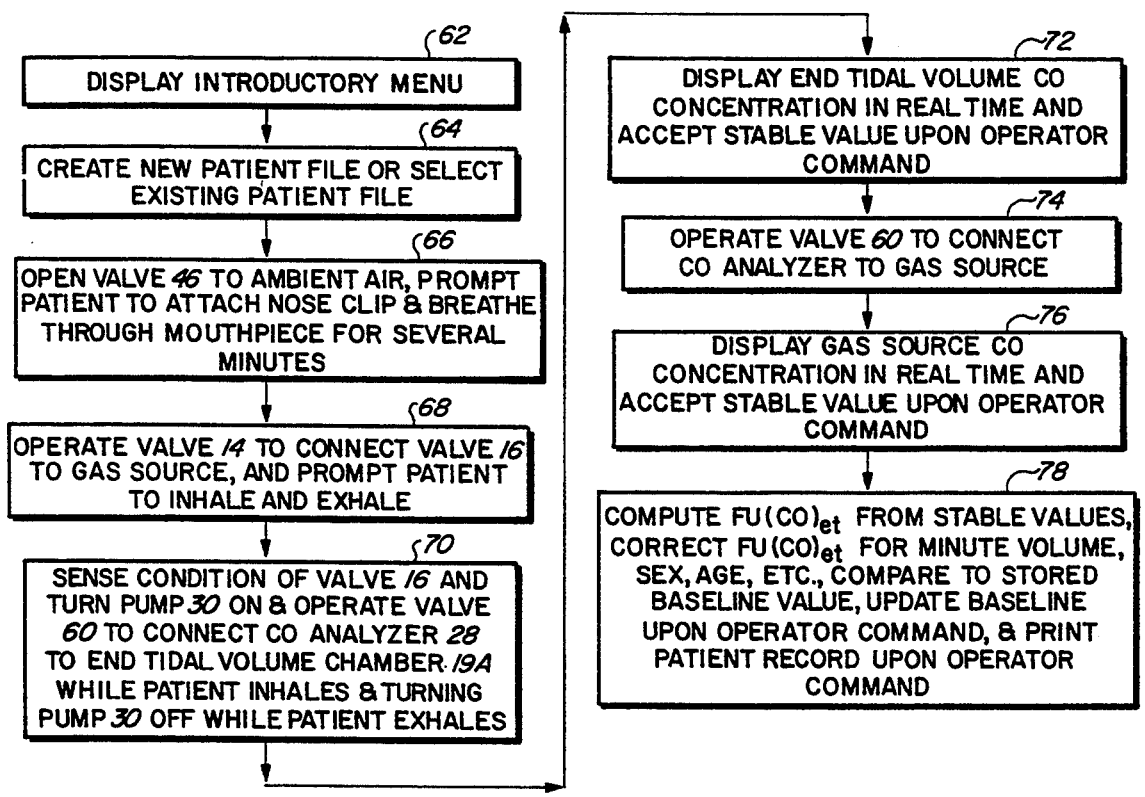
FIG. 3 is a flow chart of a program executed by the host computer of FIG. 1 to compute fractional uptake of CO, establish baseline data for each patient, and compare it to subsequent test results.

The procedure executed by host processor 35 is indicated in the flow chart of FIG. 3. Initially, host processor 35 displays an introductory menu, as indicated in block 62. As indicated in block 64, the operator selects an existing patient file, an option to create a new patient file for a new patient, or an option for calibrating the system of FIG. 1. Next, host processor 35 opens valve 14 to ambient air, prompts the operator to attach nose clips to the patient to be tested and cause the patient to breathe through mouthpiece 18 long enough (several minutes) to become comfortable with the machine, as indicated in block 66. Next, host processor 35 actuates valve 14 to couple non-rebreather valve 16 to gas reservoir 12 and gas source 10 and prompts the patient to inhale and exhale, as indicated in block 68. Then, as indicated in block 70, host processor 35 responds to sensing the condition of non-rebreather valve 16 and turns pump 30 on while the patient inhales, and turns pump 30 off while the patient exhales. Host processor 35 operates 4-way valve 60 to couple CO analyzer 28 to end tidal volume chamber 19A while the patient inhales, so that the end tidal volume of last exhaled air is drawn through CO analyzer 28 and host processor 35 continually reads in real time the values of CO concentration produced thereby.

Figure 3A:
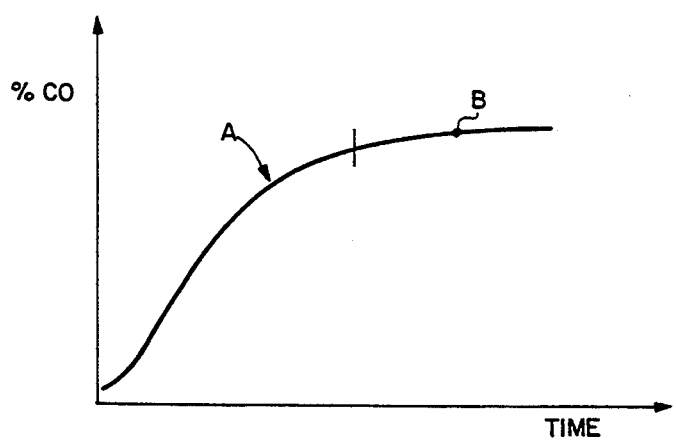
FIG. 3A is a graph useful in describing the flow chart of FIG. 3.

As indicated in block 72, host processor 35 displays in real time the concentration of CO in the end tidal volume of air being drawn through CO analyzer 28, as shown in FIG. 3A. Host processor 35 "accepts" as stable a value B of the CO concentration in the end tidal volume the present value when the operator so commands on the basis of viewing a plot A of the CO concentration, as shown in FIG. 3A. The end tidal CO concentration generally rapidly approaches a steady state value within about thirty seconds.

Next, as indicated in block 74, host computer 35 operates valve 60 to couple CO analyzer 28 to gas source 10 and accept a stable real time reading of that concentration when the operator so commands via the keyboard of host computer 35. Then, in block 78 host computer 35 computes the fractional uptake $FU(CO)_{et}$ from the stable readings previously obtained and compares it to the patient's baseline $FU_{CO}$ reading. The computed value of $FU(CO)_{et}$ then is, in essence, corrected to account for the patient's present minute volume and his or her age, sex, and possibly other factors. Host computer 35 also updates the patient's baseline if the operator so indicates, or, if it is a new patient, creates a new baseline file for the patient. Upon command, host processor 35 prints out a patient record, if the operator so commands.

Figure 4:
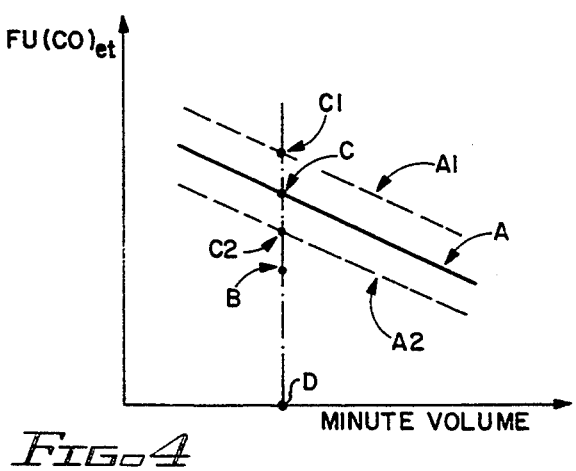
FIG. 4 is a graph of end tidal volume fractional uptake verses minute volume, useful in explaining the invention.

FIG. 4 shows how the $FU(CO)_{et}$ value is, in essence, corrected for the patient's present minute volume. In FIG. 4, A designates a linear regression curve. Linear regression curve A preferably is previously obtained for the patient when he or she is healthy, and therefore represents "normal" values of $FU(CO)_{et}$ as a function of the patient's minute volume when linear regression curve A is obtained. Curves A1 and A2 designate upper and lower boundaries of values of $FU(CO)_{et}$ which are within a standard deviation of linear regression line A.

The patient's present value of $FU(CO)_{et}$ is represented by point B, for which the measured and computed minute volume is represented by point D. The value of $FU(CO)_{et}$ of point B then is compared to that of point C on the patient's prior linear regression line A for the same minute volume as point B. In the example shown in FIG. 4, point B is more than a standard deviation below point C, ie, below point C2. This indicates an abnormally low value of $FU(CO)_{et}$ for the patient at the present time.

If no linear regression line as shown in FIG. 4 has been obtained for the patient, then the present reading represented by point B can be compared with a previously determined population linear regression line similar to A for a population of people who have been previously tested. On that basis, conclusions can be made about the meaning of the patient's present fractional uptake reading.

It is believed that the protocol for use of an economical, portable instrument as in FIG. 1 for measurement of the fractional uptake $FU(CO)_{et}$ should depend on the patient's stage of the disease. Patients who are HIV positive but asymptomatic should have three to five consecutive measurements to establish a baseline. Then measurements should be made routinely every month to maintain and update baseline data. The patient should be immediately tested if he or she has complaints of a pulmonary nature, unexplained body temperature increases, increased malaise, or fatigue. Patients with a prior episode of PCP pneumonia or T cell measurements of less than 200 who are on inhaled pentamidine could be conveniently tested routinely just before their regular drug treatments.

The system shown in FIG. 1 is inexpensive, small, and light. Mouthpiece 18, valve 16, and exhaled gas collection bag 20 can be inexpensive disposable items, to minimize the need to sterilize the entire machine before and after each use.

The system therefore can be provided in an outpatient setting or wherever needed and used frequently for each AIDS patient being treated. The initial use is to establish a "baseline" reading of the percentage of CO gas uptake before the patient contracts pneumonia.

The value of $FU(CO)_{et}$ is easier to measure than the traditional measures of diffusion capacity. The use of end tidal volume is an important concept in allowing for the development of the portable instrumentation described herein. Important implications of this measure are that the dead volume of the instrument is no longer a concern. It is no longer a requirement to collect all of a subject's expired breath. The measurement of the value of $FU(CO)_{et}$ can be obtained faster than previous methods of measuring fractional uptake, and the measurement of $FU(CO)_{et}$ is highly reproducible with typical coefficient of variations of less than 5%. However, it is required that a measure of minute volume at the time of the test be recorded.

While the invention has been described with reference to several particular embodiments thereof, those skilled in the art will be able to make the various modifications to the described embodiments of the invention without departing from the true spirit and scope of the invention. It is intended that all combinations of elements and steps which perform substantially the same function in substantially the same way to achieve the same result are within the scope of the invention. For example, the fractional uptake measurement method and apparatus of the present invention can be utilized to enable a physician to better judge appropriate amounts and durations of administering various drugs in treatment of PCP pneumonia by closely monitoring the patient's fractional uptake of carbon monoxide and decreasing or discontinuing the drug treatment as soon as the present measurements return or approach the patient's previously established baseline value. The described system could be modified to provide readouts of the actual concentration in a persons exhaled breath, rather than the fractional uptake. A patient or worker baseline concentration may be established, or a population norm baseline may be established. The concentration of carbon monoxide in the patient's or worker's exhaled breath may then be measured and compared with the appropriate baseline to determine if unacceptable amounts of carbon monoxide are being inhaled by the patient or worker, for example by smoking cigarettes or breathing contaminated air in a workplace. (The inhaling of the 0.1% CO containing air and the fractional uptake computation then are not necessary.) An increase of CO in a person's exhaled breath can accurately indicate inhalation of tobacco smoke up to 8 to 12 hours earlier. Patients who take certain medications experience lung damage as a side effect. For example, recipients of transplanted hearts, kidneys, and other organs which are not well matched to the recipient must take drugs that suppress their immune systems to prevent the immune system from rejecting the transplanted organ. Such transplant recipients are susceptible to PCP pneumonia, so early detection of diminishing lung function is as important for them as the case for HIV positive patients. Such damage can be monitored using the method and apparatus of the present invention by first establishing baselines of such patients and then continuing to compare current fractional uptake measurement of lung function to such baselines.

What is claimed is:

1. A method of measuring lung function, comprising the steps of:
   (a) supplying air containing a first concentration of CO from a gas source into a tube;
   (b) opening a first path in a first valve device to allow the air supplied to the tube to be inhaled by a patient through the first valve device and a mouthpiece;
   (c) closing the first path to allow air exhaled by the patient to flow through a second path in the first valve device into a gas containing volume;
   (d) measuring the CO concentration of air supplied by the gas source by passing some of the supplied air into a CO analyzer and operating the CO analyzer to produce a first signal representing the concentration of CO in the supplied air and converting the first signal to a first number representing the concentration of CO in the supplied air;
   (e) measuring the CO concentration of air exhaled by the patient by passing some of the exhaled air from the gas containing volume into the CO analyzer to produce a second signal representing the concentration of CO in the exhaled air and converting the second signal to a second number representing the concentration of CO in the exhaled air;
   (f) computing a fractional uptake of CO from the first and second numbers; and
   (g) comparing the fractional uptake with a previously stored baseline value.

2. The method of claim 1 including, before step (f), measuring the rate of flow of air exhaled by the patient, wherein the computing of step (f) includes using information based on the measured rate of flow.

3. The method of claim 2 wherein the opening of the first path in step (b) is in response to inhaling by the patient.

4. The method of claim 3 where the closing of the first path in step (c) is in response to exhaling by the patient.

5. The method of claim 4 including repeating steps (a), (b), (c), (e), (f), and (g) for other inhaling and other exhaling by the patient.

6. The method of claim 5 wherein the passing of exhaled air from the gas containing volume includes passing an end tidal volume of air last exhaled by the patient from the gas containing volume into the CO analyzer by turning on a pump coupled to the CO analyzer while the second path is closed.

7. The method of claim 2 including diagnosing the patient as likely to be infected with PCP pneumonia if the present fractional uptake is less than the stored baseline value by a predetermined amount.

8. The method of claim 2 wherein the CO concentration of air supplied by the gas source is approximately 0.1%.

9. The method of claim 2 wherein step (a) includes supplying the air from a gas source through a regulator actuated in response to suction produced at the mouthpiece by inhaling by the patient.

10. The method of claim 2 wherein steps (f) and (g) are performed by a computer, step (f) including computing the fractional uptake of carbon monoxide according to the expression $$1 - \frac{F_A}{F_I}$$

where $F_I$ is the percentage concentration of CO in the gas supplied by the gas source and $F_A$ is the percentage of CO in the end tidal volume of gas exhaled.

11. An apparatus for measuring lung function, comprising in combination:
(a) a gas source for supplying air containing a particular concentration of CO gas;
(b) a mouthpiece;
(c) a chamber for temporarily storing exhaled air;
(d) a non-rebreather valve device coupled to the gas source, the chamber, and the mouthpiece and including a first valve path to selectively allow air from the gas source to be inhaled through the mouthpiece by a patient and preventing air exhaled by the patient from returning to the gas source, the non-rebreather valve device also including a second valve path to selectively allow air exhaled by the patient to pass into the chamber;
(e) a CO analyzer;
(f) means for passing air from the gas source into the CO analyzer to cause the CO analyzer to produce a first signal representing the concentration of CO in air supplied by the gas source;
(g) means for passing some of the exhaled air in the chamber into the CO analyzer, causing the CO analyzer to produce a second signal representing the concentration of CO in the exhaled air;
(h) an analog-to-digital converter coupled to the CO analyzer a operating to convert the first and second signals into first and second digital numbers representing the CO concentrations in the air supplied by the gas source and the air exhaled by the patient, respectively;
(i) means for computing a fractional uptake of CO from the first and second digital number; and
(j) means for comparing the fractional uptake with a stored baseline value.

12. The apparatus of claim 11 including means for measuring a rate of flow of air exhaled by the patient and means responsive thereto for computing a minute volume for the patient.

13. The apparatus of claim 12 wherein the chamber has a volume at least equal to an end tidal volume.

14. The apparatus of claim 13 wherein the particular concentration of CO from the gas source is approximately 0.1%.

15. The apparatus of claim 14 including a pump coupled to a gas outlet of the CO analyzer, and means for turning on the pump in response to suction produced at the mouthpiece by the patient to produce a negative pressure at the gas outlet of the CO analyzer to draw the end tidal volume of exhaled gas in a portion of tube through the CO analyzer.

16. The apparatus of claim 15 wherein the gas source includes a gas bottle and a regulator connected to the gas bottle and actuated by suction produced at the mouthpiece by the patient.

17. The apparatus of claim 15 wherein the computing means is included in a host computer which computes the fractional uptake of carbon monoxide according to the equation $$1 - \frac{F_A}{F_I}$$

where $F_I$ is the CO percentage concentration of gas to be inhaled from the gas source and $F_A$ is the CO percentage concentration of an end tidal volume of gas exhaled.

18. An apparatus for measuring lung function, comprising in combination:
(a) a gas source of air containing a particular concentration of CO gas;
(b) a mouthpiece;
(c) a chamber for temporarily storing exhaled air;
(d) a non-rebreather valve device coupled to the gas source, the chamber, and the mouthpiece and including a first valve path to selectively allow air from the gas source to be inhaled through the mouthpiece by a patient and prevent air exhaled by the patient from returning to the gas source, the non-rebreather valve device also including a second valve path to selectively allow air exhaled by the patient to pass into the chamber;
(e) a CO analyzer;
(f) a first conduit coupling the gas source and the CO analyzer to pass air from the gas source into the CO analyzer, the CO analyzer producing a first signal representing the concentration of CO in air from the gas source;
(g) a second conduit coupling the chamber and the CO analyzer to pass some of the exhaled air in the chamber into the CO analyzer, the CO analyzer producing a second signal representing the concentration of CO in the exhaled air;
(h) an analog-to-digital converter coupled to the CO analyzer a operating to convert the first and second signals into first and second digital numbers representing the CO concentrations in the air supplied by the gas source and the air exhaled by the patient, respectively; and
(i) a computing device coupled to the analog-to-digital converter and adapted to compute a fractional uptake of CO from the first and second digital numbers and compare the fractional uptake with a stored baseline value.

19. The apparatus of claim 18 including a pneumotachometer device coupled to the chamber and the computing device, the computing device being adapted to compute a minute volume for the patient.

20. The apparatus of claim 19 wherein the chamber has a volume at least equal to an end tidal volume.

21. The apparatus of claim 18 including a pump coupled to a gas outlet of the CO analyzer and to the computing device, the computing device being adapted to turn on the pump in response to suction produced at the mouthpiece by the patient to produce a negative pressure at the gas outlet of the CO analyzer to draw the end tidal volume of exhaled gas in a portion of tube through the CO analyzer.

22. The apparatus of claim 21 wherein the gas source includes a gas bottle and a regulator connected to the gas bottle and actuated by suction produced at the mouthpiece by the patient.

23. The apparatus of claim 21 wherein the computing device is included in a host computer which computes the fractional uptake of carbon monoxide according to the equation $$1 - \frac{F_A}{F_I}$$

where $F_I$ is the CO percentage concentration of gas to be inhaled from the gas source and $F_A$ is the CO percentage concentration of an end tidal volume of gas exhaled.

* * * * *